United States Patent [19]

McRae

[11] Patent Number: Plant 6,573

[45] Date of Patent: Jan. 31, 1989

[54] LILY PLANT NAMED 'FIRE PIXIE'

[75] Inventor: Edward A. McRae, Boring, Oreg.

[73] Assignee: Melridge, Inc., Aurora, Oreg.

[21] Appl. No.: 63,927

[22] Filed: Jun. 19, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new variety of hybrid lily plant bearing large clusters of flowers particularly characterized by their vivid orange to orange-red coloration and their comparatively inconspicuous spots, the flowers being of medium size, excellent form and borne with an upright orientation. The plant itself is of short stature with moderately long and full leaves which, with its upright prolific flower production, makes it especially suitable as a pot plant variety; its color pattern and silhouette being completely new in the upright Asiatic divisions of lilies suited to forcing and to mass commercial cultivation. The plant is also highly resistant to disease and shows a high tolerance of virus, making it an excellent garden plant, and its bulbs may be precooled and forced throughout the year for pot plant production.

1 Drawing Sheet

BACKGROUND OF THE INVENTION

This new variety of lily plant originated as a seedling selected from a group of seedlings planted by me at Sandy, Ore., with seeds of a hybrid which resulted from my breeding efforts carried on with the object of producing new lily plants having blooms in the shades of orange and red, well suited for forcing for pot plant production out-of-season. The parent hybrid for this selected seedling was developed by me using a very short, cream-flowered clonal selection from the 'Pastel Hybrids' strain as the seed parent and using the clonal cultivar 'Red Carpet' (unpatented) as the pollen parent.

This particular seedling was selected for propagation because its flowers were characterized by a medium size, vivid orange to orange-red coloration, and an inconspicuous "ring" of very tiny spots parallel with the nectaries on each tepal and surrounding the center of the bloom, a color pattern unique in this type of lily, and asexual propagation of this selected seedling was done by me and under my direction at Sandy, Ore., by bulb scales and also by natural propagation from bulblets. Because the propagated plants appeared to possess all of the desired characteristics of excellence of form, color and habit, further propagation through several successive generations was carried on at Sandy, Ore., under my direction, which demonstrated clearly that the novel characteristics of my selected seedling would hold true from generation to generation and appeared to be firmly fixed.

I have found that this new variety remains short and is not overly susceptible to bud abortion when forced into flower out-of-season as a pot plant and, in addition, the clone possesses to a high degree the desirable characteristics of hybrid vigor, great hardiness, and disease resistance. Also, the clone is vigorous and a good grower and propagator as observed at Sandy, Ore. I have also found that the new plant is well suited to forcing out-of-season when the bulbs are dug at the appropriate time and properly precooled. For example, October-dug bulbs, properly precooled and potted in January, will flower under glass in western Oregon in an average of sixty-five to seventh-five days, with no supplementary lighting and at moderate greenhouse temperatures.

DESCRIPTION OF THE DRAWING

This new variety of lily plant is illustrated by the accompanying photographic drawing, which shows the open bloom in full color and illustrates the flower form and tepal arrangement, as well as the novel and distinctive orange to orange-red flowers marked with inconspicuous tiny spots which form the "ring" of spots around the center of the flower, the colors shown being as close to those specified herein as is reasonably possible to obtain by conventional photographic procedures.

DESCRIPTION OF THE NEW VARIETY

The following is a detailed description of my new variety of Asiatic hybrid lily, with nomenclature according to The International Lily Register of The Royal Horticultural Society of London, Second Edition, 1969; and the color designations herein are according to The R.H.S. Colour Chart published by The Royal Horticultural Society in 1966.

THE PLANT

Origin: Seedling.

Parentage:

*Seed parent.*—A short, cream-flowered clonal selection of the 'Pastel Hybrids' strain.

*Pollen parent.*—Lilium 'Red Carpet' (unpatented).

Classification:

*Botanic.*—Division I-A, upright Asiatic hybrid lily, The Royal Horticultural Classification of Lilies (The Royal Horticultural Society of London, England).

*Commercial.*—Hybrid Lilium Clone.

Form: Single stem, erect and stately.

Height: About 30 to 35 cm. on stems produced by glasshouse forcing of bulbs of about 12 to 18 cm. in circumference, provided that their light levels are adequate; low light levels may cause "stretching".

Growth: Vigorous and upright.

Foliage:

*Quantity.*—Abundant.

*Size of leaf.*—About 7 to 10 cm. long and about 0.5 to 1 cm. wide.

*Leaf shape.*—Lanceolate with acuminate tip and entire margins.

*Texture.*—Leathery.

*Aspect.*—Glossy.

*Color.*—Dark green, somewhat lighter on the bottom side.

The bulb:

*Size.*—Various, ranging up to about 25 cm. in circumference as commercially used.

*Color.*—White.

THE BUD

Form: Long ovoid with obtuse apex and rounded base.

Size: About 8 to 9 cm. long and about 6 cm. in circumference just prior to opening.

Opening rate: The bud opens slowly, taking about one hour in response to morning light.

Color: Medium Orange, 28C/D, with a flush of green along the midribs and at the tip prior to opening and as the tepals being to unfurl.

Peduncle:

*Length.*—Averages about 4 to 6 cm. The peduncle may elongate if light levels are too low or if the bulbs have been improperly stored prior to forcing.

*Color.*—Medium green.

THE FLOWER

Blooming habit: Once annually and profusely in midseason.

Size: The blooms average about 12 to 15 cm. in diameter.

Borne: In a single compact raceme comprising about nine to eleven buds from a bulb of about 12 to 16 cm. in circumference.

Shape: Cup-shaped upon first opening and flattening as the tepals recurve on the second day.

Tepalage: Normal, with six imbricated tepals in hexagonal arrangement.

*Size of tepals.*—Outer tepals average about 2.5 cm. wide. Inner tepals average about 3 cm. wide.

*Color.*—The base color is Orange, 28B, at the center of each tepal suffusing laterally to Orange-Red, 30A, at the tepal margins. There is a flush of deeper Red, 35A/B, which is about 1 to 2 mm. wide parallel with the nectaries and a 3 mm. wide band of the same color along the margins of the basal 5 cm. of each tepal. The nectaries are deep orange overlaid with white pubescence.

*Spotting.*—Each of the tepals carries about ten to twenty tiny, inconspicuous spots disposed adjacent the nectaries.

*Aspect.*—Shiny.

*Longevity.*—The tepals stay on the stem about three weeks.

Pedicel:

*Length.*—About 4 to 8 cm., in average.

*Color.*—Medium to dark green.

*Character.*—Sturdy and ascending up to about 60 degrees from the horizontal.

Color changes: The flower may become slightly less red and more orange as it ages, depending upon light levels; usually there is only a slight color change if the light levels are adequate for cut flower and pot plant maintenance.

Fragrance: None.

Disease resistance: The flowers and plant are resistant to disease; in particular, they are resistant to Fusarium bulb rot and Botyrutis blight.

Lasting quality: The flower is long lasting, both of the plant and as a cut flower.

REPRODUCTIVE ORGANS

Stamens:

Number.—Six, with arrangement typical of genus Lilium.

*Anthers (dehisced) and pollen.*—Color — greyed, orange, 169A to 171A.

*Filaments.*—Length: About 5 cm. Color: Soft Red, 180B/C.

Pistil:

*Number.*—One.

*Length.*—About 5 cm.

*Stigma.*—Size: Medium, about 2 to 3 mm. wide. Color: Greyed Purple, 187B.

Character of ovary: The ovary is characteristic of the genus Lilium.

THE FRUIT

Fertility: The fruit is fertile.

Shape: Ovoid.

Color at maturity: Soft brown, sometimes overlaid with soft plum.

This new lily most closely resembles 'Red Carpet' but it has an orange to red-orange coloration unlike the deeper red-orange color of 'Red Carpet'. The new plant also has a more compact inflorescence with shorter pedicels, a higher bud count, a shorter height, and with shorter leaves than 'Red Carpet'. Also, the flowers of this new variety have broader and more pointed tepals than 'Red Carpet' and carry an inconspicuous ring of tiny spots. The plant is also more reliable and uniform in its forcing performance and it can be forced into flower much more rapidly than 'Red Carpet'; and it has green stems and pedicels, unlike the "black" stems of 'Red Carpet'.

I claim:

1. The new and distinct variety of Asiatic hybrid lily plant and parts thereof substantially as herein shown and described, characterized by its orange to red-orange flowers with their inconspicuous ring of tiny spots encircling the center of the bloom; by its versatility both as a garden plant and as a pot plant variety suited for forcing into flower out-of-season; and by its short stemmed and abundantly leaved, upright-flowering silhouette.

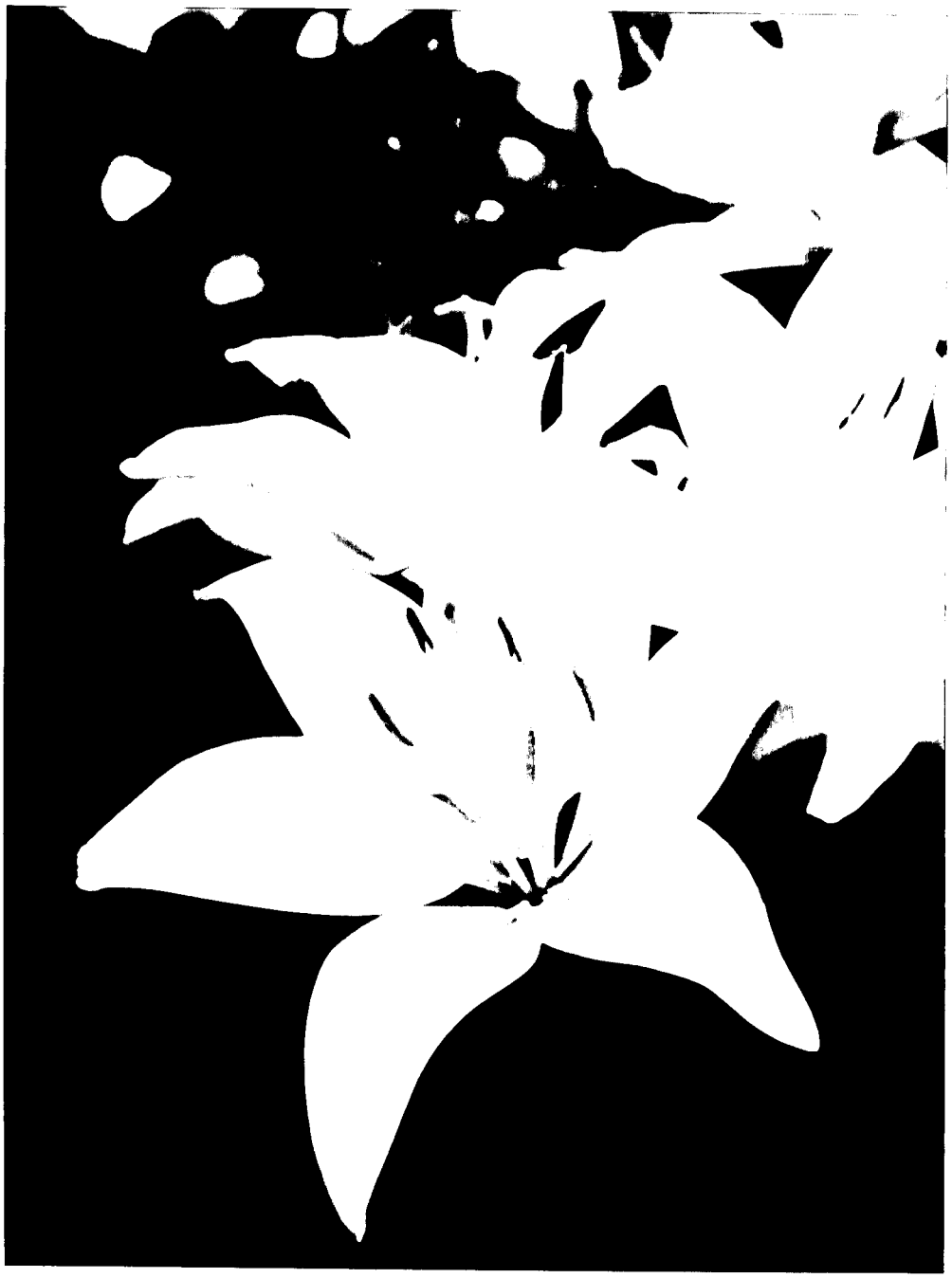

* * * * *